United States Patent [19]

Mack et al.

[11] Plant 4,004

[45] Jan. 4, 1977

[54] CHRYSANTHEMUM PLANT

[75] Inventors: Grace H. Mack, New Canaan, Conn.; William E. Duffett, Akron; Walter H. Jessel, Jr., Doylestown, both of Ohio

[73] Assignee: Yoder Brothers, Inc., Barberton, Ohio

[21] Appl. No.: 658,851

[22] Filed: Feb. 18, 1976

[51] Int. Cl.$^2$ ..... A01H 5/00

[52] U.S. Cl. ..... Plt./75

[58] Field of Search ..... Plt./75, 78

*Primary Examiner*—Robert E. Bagwill
*Attorney, Agent, or Firm*—Donald D. Jeffery

CLAIM

A new and distinct cultivar of chrysanthemum known by the cultivar name Nuggets and characterized particularly as to uniqueness by the combined characteristics of flat inflorescence form; pompon inflorescence type; golden yellow inflorescence color; diameter across face of inflorescence from 1.25 to 1.5 inches; permanence of inflorescence ranging from 14 to 21 days; medium plant height; semi-spreading branching pattern; average natural season flowering date of October 5; and average flowering response period of 7 weeks in photoperiodic controlled flowering programs.

3 Drawing Figures

The present invention comprises a new and distinct cultivar of *Chrysanthemum morifolium*, Ramat., hereinafter referred to by the cultivar name Nuggets (No. 73002M01).

Nuggets is a product of a planned breeding program which had the objective of creating cultivars with small pompon inflorescence type, short height, spreading branching pattern, durable inflorescence, short (6 to 7 weeks) flowering response period, and adaptability to both natural season outdoor flowering and controlled greenhouse flowering programs.

Nuggets was originated from a cross made by Grace H. Mack in a controlled breeding program in New Canaan, Conn. in the year 1972. The female, or seed parent, was 5-70 (No. 21730E03; unnamed seedling), a yellow pompon originated by the present inventors from a cross between two unnamed seedlings, identified as C163 and 669. The male, or pollen parent, of Nuggets was C62-66 (No. 21730E04; unnamed seedling), a white pompon of parentage unknown to the present inventors.

Nuggets was discovered and selected as a flowering plant within the progeny of the stated cross by Walter H. Jessel, Jr. on May 2, 1973 in an outdoor field in Ft. Myers, Fla.

The first act of asexual reproduction of Nuggets was accomplished when vegetative cuttings were taken from the initial selection in June, 1973 in a controlled environment in Barberton, Ohio by a technician working under formulations established and supervised by William E. Duffett and Walter H. Jessel, Jr. Horticultural examination of selected units initiated Oct. 11, 1973 has demonstrated that the combination of characteristics as herein disclosed for Nuggets are firmly fixed and are retained through successive generations of asexual reproduction.

Nuggets has not been observed under all possible environmental conditions. The phenotype may vary significantly with variations in environment such as temperature, light intensity, and daylength. The following observations, measurements, and comparisons describe plants grown in a field in Barberton, Ohio under outdoor conditions which are generally described in *Local Climatological Data, Annual Summary With Comparative Data, Akron, Ohio*. U.S. Department of Commerce, National Oceanic and Atmospheric Administration, Environmental Data Service, Washington, D.C., 1973, 1974, 1975 and *Tables of Sunrise, Sunset, and Twilight*. Supplement to the American Emphemeris, 1946. U.S. Naval Observatory, Washington, D.C., pg. 103. When an environment divergent from that described was utilized to more clearly define a trait, that environment is specified.

The following traits have been repeatedly observed and are determined to be basic characteristics of Nuggets which in combination distinguish this crysanthemum as a new and distinct cultivar:

1. Flat inflorescence form.
2. Pompon inflorescence type.
3. Golden yellow inflorescence color.
4. Diameter across face of inflorescence from 1.25 to 1.5 inches.
5. Permanence of inflorescence ranging from 14 to 21 days.
6. Medium plant height.
7. Semi-spreading branching pattern.
8. Average natural season flowering date of Oct. 5.
9. Average flowering response period of 7 weeks in photoperiodic controlled flowering programs.

The accompanying photographic drawings show typical inflorescence and foliage characteristics of Nuggets with colors being as nearly true as possible with illustrations of this type. Sheet 1 is a color photograph of Nuggets. Sheet 2 is a black and white photograph showing three views of the inflorescence of Nuggets. Sheet 3 is a black and white photograph showing the foliage of Nuggets at three stages of growth.

Of the many commercial cultivars known to the present inventors, the most similar existing cultivar in comparison to Nuggets is Goldtone (No. 21670E13; U.S. Plant Pat. No. 3,276).

Reference is made to attached Chart A which compares certain characteristics of Nuggets with the same characteristics of Goldtone. General comparisons are as follows.

In comparison to Goldtone, Nuggets has different inflorescence type, taller plant height, earlier natural season flower date, more spreading branching pattern, and smaller diameter across face of inflorescence. The inflorescence color, inflorescence form, and controlled flowering response of Nuggets are similar to those of Goldtone.

In the following description, color references are made to The Munsell Limit Color Cascase, 1972 edition. The color values were determined between 10:30 and 11:00 A.M. on Oct. 14, 1975 under 120 foot-candle light intensity at Barberton, Ohio.

Botanical Classification: *Chrysanthemum morifolium*, Ramat., cv Nuggets.

I. INFLORESCENCE

A. Capitulum:

*Form.*—flat.
*Type.*—pompon.
*Permanence.*—14–21 days.
*Diameter across face.*—1.25 to 1.5 inches.

B. Corolla of ray florets:

*Texture (adaxial).*—glabrous.
*Appearance and form.*—ligulate.
*Arrangement.*—whorled on receptacle
*Persistence.*—resists shatter.
*Color (abaxial).*—26–4 to 26–6
*Color (adaxial).*—26–3 to 26–6.

C. Reproductive Organs:

*Androecium.*—present disc florets only; scant pollen.
*Gynoecium.*—present both ray and disc florets.

II. PLANT

A. General appearance: semi-spreading; medium height.
B. Duration and texture: perennial; herbaceous.
C. Foliage:

*Color (abaxial).*—21–13 to 21–14.
*Color (adaxial).*—21–12 overlaid with white.
*Shape.*—spatulate; moderately lobed.
*Texture.*—glabrous.
*Arrangement.*—alternate.
*Venation.*—prominent.
*Margin.*—moderately serrated.

CHART A

COMPARISON OF NUGGETS AND GOLDTONE

| CULTIVAR | INFLORESCENCE COLOR | INFLORESCENCE FORM AND TYPE | PLANT HEIGHT | AVERAGE NATURAL SEASON FLOWER DATE | BRANCHING PATTERN | CONTROLLED FLOWERING RESPONSE | DIAMETER ACROSS FACE OF INFLORESCENCE |
|---|---|---|---|---|---|---|---|
| Nuggets | Golden yellow | Flat Pompon | Medium from 13 to 14 inches | October 5 | Semi-spreading | 7 week | 1.25 to 1.5 inches |
| Goldtone | Golden yellow | Flat Decorative | Short from 10 to 12 inches | October 8 | Semi-upright | 7 week | 2.0 to 2.5 inches |

COMPARISONS MADE OF PLANTS GROWN UNDER NATURAL SEASON OUTDOOR FIELD CONDITIONS IN BARBERTON, OHIO.

We claim:

1. A new and distinct cultivar chrysanthemum known by the cultivar name Nuggets and characterized particularly as to uniqueness by the combined characteristics of flat inflorescence form; pompon inflorescence type; golden yellow inflorescence color; diameter across face of inflorescence from 1.25 to 1.5 inches; permanence of inflorescence ranging from 14 to 21 days; medium plant height; semi-spreading branching pattern; average natural season flowering date of Oct. 5; and average flowering response period of 7 weeks in photoperiodic controlled flowering programs.

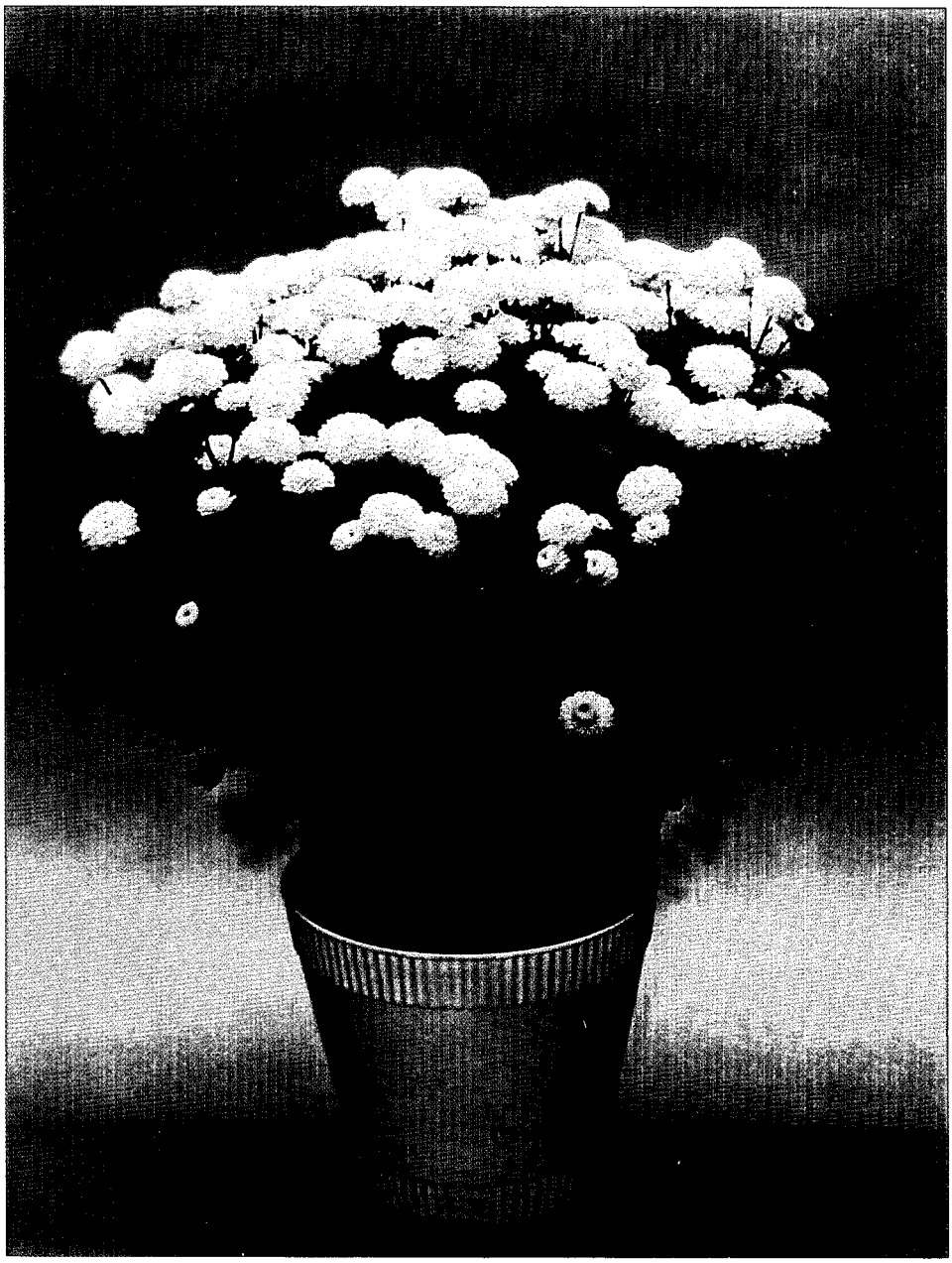

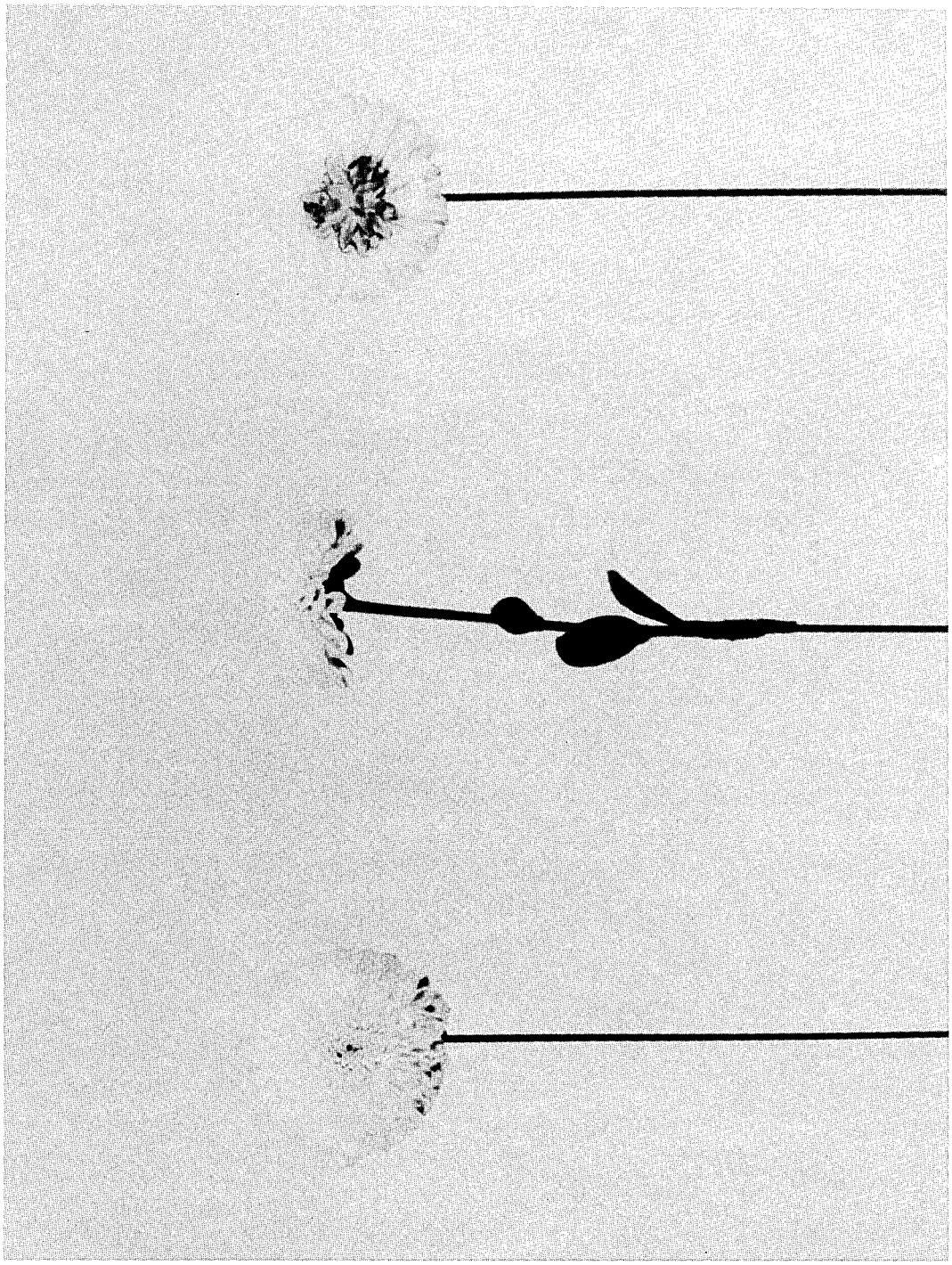

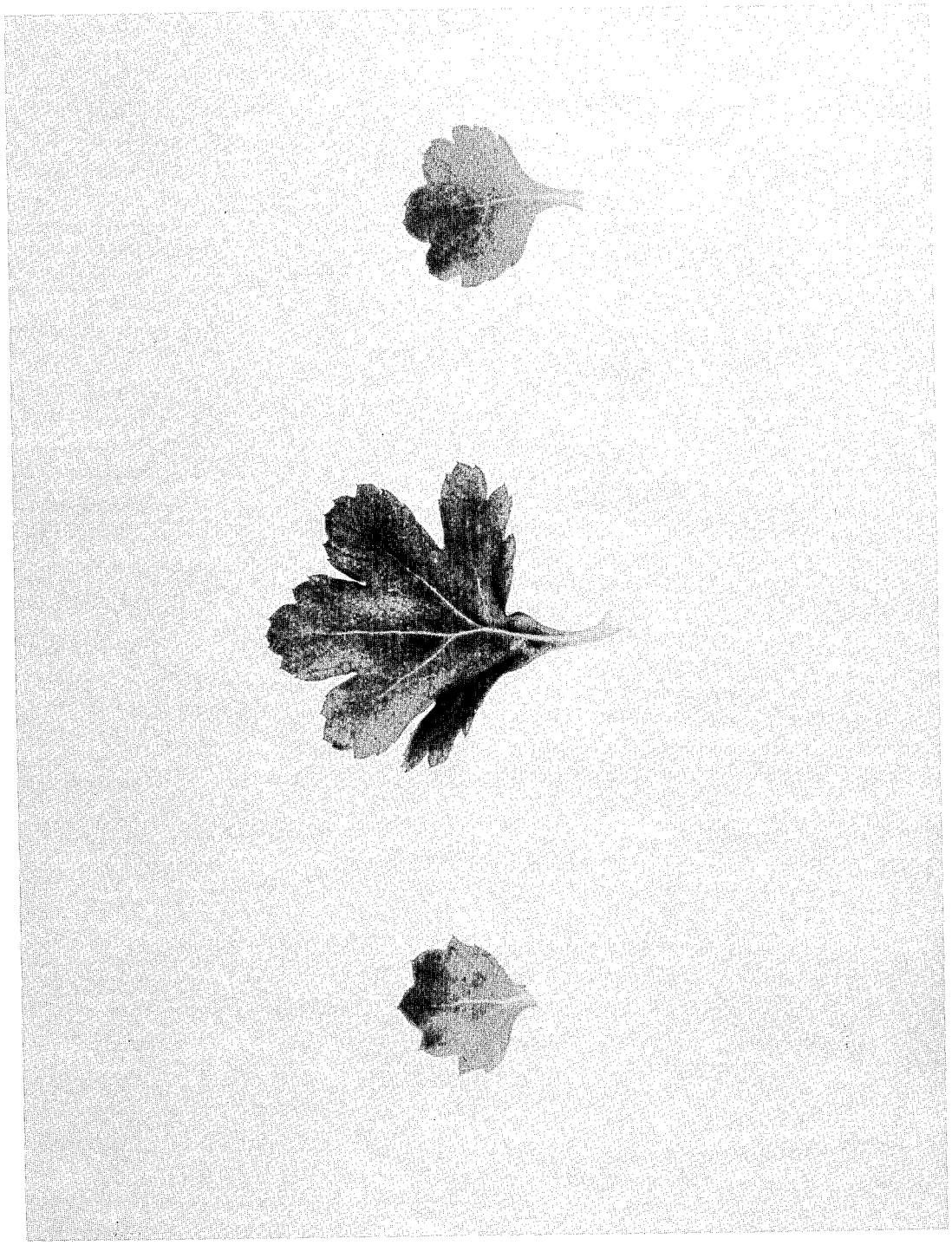

* * * * *